US008137302B2

(12) United States Patent
Aljuri et al.

(10) Patent No.: US 8,137,302 B2

(45) Date of Patent: Mar. 20, 2012

(54) METHODS AND SYSTEMS FOR OCCLUDING COLLATERAL FLOW CHANNELS IN THE LUNG

(75) Inventors: Nikolai Aljuri, Revere, MA (US); Jose G. Venegas, Swapscott, MA (US); Ajit Nair, Milipitas, CA (US); Rodney C. Perkins, Woodside, CA (US)

(73) Assignee: Pulmonx Corporation, Redwood City, CA (US)

(*) Notice: Subject to any disclaimer, the term of this patent is extended or adjusted under 35 U.S.C. 154(b) by 1247 days.

(21) Appl. No.: 11/684,950

(22) Filed: Mar. 12, 2007

(65) Prior Publication Data

US 2008/0228130 A1 Sep. 18, 2008

(51) Int. Cl.
*A61M 16/00* (2006.01)

(52) U.S. Cl. ........................................................ 604/24

(58) Field of Classification Search .................... 604/23, 604/24, 25, 26; 128/203.12, 207.14
See application file for complete search history.

(56) References Cited

U.S. PATENT DOCUMENTS

| | | | | |
|---|---|---|---|---|
| 5,972,026 | A | 10/1999 | Laufer et al. | |
| 6,083,255 | A | 7/2000 | Laufer et al. | |
| 6,258,100 | B1 | 7/2001 | Alferness et al. | |
| 6,287,290 | B1 | 9/2001 | Perkins et al. | |
| 6,398,775 | B1 | 6/2002 | Perkins et al. | |
| 6,527,761 | B1 | 3/2003 | Soltesz et al. | |
| 6,585,639 | B1 | 7/2003 | Kotmel et al. | |
| 6,679,264 | B1 | 1/2004 | Deem et al. | |
| 6,709,401 | B2 | 3/2004 | Perkins et al. | |
| 6,878,141 | B1 | 4/2005 | Perkins et al. | |
| 6,997,918 | B2 | 2/2006 | Soltesz et al. | |
| 7,412,977 | B2 * | 8/2008 | Fields et al. | 128/200.24 |
| 7,686,013 | B2 * | 3/2010 | Chang et al. | 128/200.24 |
| 2001/0051899 | A1 | 12/2001 | Kawashima et al. | |
| 2002/0062120 | A1 | 5/2002 | Perkins et al. | |
| 2003/0228344 | A1 * | 12/2003 | Fields et al. | 424/423 |
| 2004/0016435 | A1 | 1/2004 | Deem et al. | |
| 2005/0039754 | A1 * | 2/2005 | Simon | 128/207.14 |
| 2005/0066974 | A1 * | 3/2005 | Fields et al. | 128/207.14 |
| 2005/0187561 | A1 | 8/2005 | Lee-Sepsick et al. | |
| 2005/0196344 | A1 * | 9/2005 | McCutcheon et al. | 424/45 |
| 2006/0283462 | A1 | 12/2006 | Fields et al. | |
| 2007/0186932 | A1 * | 8/2007 | Wondka et al. | 128/207.15 |
| 2007/0225747 | A1 * | 9/2007 | Perkins et al. | 606/195 |
| 2008/0027343 | A1 * | 1/2008 | Fields et al. | 600/529 |
| 2008/0249503 | A1 * | 10/2008 | Fields et al. | 604/506 |

OTHER PUBLICATIONS

International Search Report and Written Opinion of PCT Application No. PCT/US08/56292, dated Aug. 29, 2008, 7 pages total.

* cited by examiner

*Primary Examiner* — Nicholas Lucchesi
*Assistant Examiner* — Aarti B Berdichevsky
(74) *Attorney, Agent, or Firm* — Wilson Sonsini Goodrich & Rosati

(57) ABSTRACT

The lateral flow between adjacent lung segments is occluded by blocking collateral flow channels with particles. A gas flow is established from one lung segment through the flow channels in an intermediate fibrous septum, and out through the adjacent lung segment. Particles entrained in the gas flow become lodged in the collateral flow channels to eventually block flow.

17 Claims, 8 Drawing Sheets

PARTICLES ENTRAINED IN A CARRIER GAS
50
INHALE AIR
EXHALE AIR AND CARRIER
ET
10
AW1
AW2
LS1
P
LS1
FS
LS2
LS3

FIG. 7B

METHODS AND SYSTEMS FOR OCCLUDING COLLATERAL FLOW CHANNELS IN THE LUNG

BACKGROUND OF THE INVENTION

1. Field of the Invention

The present invention relates generally to medical methods and apparatus. More particularly, the present invention relates to methods and apparatus for sealing collateral passages between adjacent lung segments prior to endobronchial lung volume reduction.

Chronic obstructive pulmonary disease is a significant medical problem affecting 16 million people or about 6% of the U.S. population. Specific diseases in this group include chronic bronchitis, asthmatic bronchitis, and emphysema. While a number of therapeutic interventions are used and have been proposed, none are completely effective, and chronic obstructive pulmonary disease remains the fourth most common cause of death in the United States. Thus, improved and alternative treatments and therapies would be of significant benefit.

Of particular interest to the present invention, lung function in patients suffering from some forms of chronic obstructive pulmonary disease can be improved by reducing the effective lung volume, typically by resecting diseased portions of the lung. Resection of diseased portions of the lungs both promotes expansion of the non-diseased regions of the lung and decreases the portion of inhaled air which goes into the lungs but is unable to transfer oxygen to the blood. Lung volume reduction is conventionally performed in open chest or thoracoscopic procedures where the lung is resected, typically using stapling devices having integral cutting blades.

While effective in many cases, conventional lung volume reduction surgery is significantly traumatic to the patient, even when thoracoscopic procedures are employed. Such procedures often result in the unintentional removal of healthy lung tissue, and frequently leave perforations or other discontinuities in the lung which result in air leakage from the remaining lung. Even technically successful procedures can cause respiratory failure, pneumonia, and death. In addition, many older or compromised patients are not able to be candidates for these procedures.

As an improvement over open surgical and minimally invasive lung volume reduction procedures, endobronchial lung volume reduction procedures have been proposed. Such endobronchial lung volume reduction procedures involve the isolation, typically permanent, of one or more diseased lung segments in order to reduce the effective lung volume and increase the portion of inhaled air which is absorbed into the blood through the lungs. Minimally invasive lung volume reduction procedures typically use a catheter which is introduced through the trachea into the branching airways of the lung. A valve plug, such as an or occlusal stent, is then implanted in an airway which feeds the diseased lung segment(s). Often, more than one such blocking element can be placed at airways feeding multiple diseased lung segments. In some instances, the isolated lung segments can be aspirated or passively deflated in order to enhance closure of the diseased region. In other cases, oxygen-rich gases may be introduced in order to induce oxygen atelectasis to still further induce collapse and closure of the diseased region.

Although such minimally invasive lung volume reduction procedures have been very effective in some patients, they have been less effective in other patients where the diseased lung segments are open to adjacent healthy or diseased segments through collateral flow channels. Normally, lung segments are defined and circumscribed by a fibrous septum (wall) which prevents the flow of air or other gases from one segment into adjacent segments. In diseased patients, the walls between adjacent lung segments may be damaged and form the collateral flow channels which permit reentry of air or other gases into the "isolated" segment being treated.

For these reasons, it would be desirable to provide methods for sealing such collateral flow channels between adjacent lung segments. Such sealing methods would be particularly useful for treating patients prior to endobronchial or other lung volume reduction procedures. Thus, methods and apparatus for sealing collateral flow channels should be compatible with known protocols for occluding diseased lung segments and regions for performing lung volume reduction, including the placement of plugs and occluding members within the airways leading to such diseased lung segments and regions. At least some of these objectives will be met by the inventions described hereinbelow.

2. Description of the Background Art

Methods for performing minimally invasive and endobronchial lung volume reduction are described in the following patents and publications: U.S. Pat. Nos. 5,972,026; 6,083,255; 6,258,100; 6,287,290; 6,398,775; 6,527,761; 6,585,639; 6,679,264; 6,709,401; 6,878,141; 6,997,918; 2001/0051899; and 2004/0016435.

BRIEF SUMMARY OF THE INVENTION

The present invention provides methods and systems for occluding collateral flow between adjacent lung segments. Such occlusion relies on introducing occlusive particles into collateral flow channels which are present in the fibrous septums (walls) which are present between adjacent segments and which, when intact and healthy, prevent flow from one segment to the other. Collateral flow between adjacent segments typically occurs as the result of disease in at least one of the segments, where the disease causes at least a portion of the separating wall to become porous or perforate due to the presence of collateral flow channels therethrough. The occlusive particles will have a size or range of sizes selected to lodge in the collateral flow channels when they are carried by air or other carrier gas in a direction from one segment to the adjacent segment. Treatment may thus be effected by entraining such particles in a carrier gas which is directed to flow through the collateral flow channels, thus causing the particles to lodge in the channels and to build up and occlude the channels over time. Treatment will typically be continued until all or at least a substantial portion of the collateral flow of the air or other carrier gas has ceased.

After occlusion of the collateral flow channels has been completed, the diseased lung segment(s) can be treated by a variety of suitable endobronchial lung volume reduction methods. Usually, volume reduction of the targeted diseased lung segment will cause a contraction of the wall which had the collateral flow channels. Such contraction will tend to collapse the channel structures over the occluding particles which have been lodged therein. Such contraction will help to anchor the particles in place and prevent their dislodgement over time. Additionally or alternatively, the particles could be coated or loaded with hydrogels and other non toxic expandable hydrogel or a combination of hydrogel and drug and non toxic sealants including, hemo glue, bone glue, tissue glue, etc as well as adhesives and/or drugs to induce permanent closure of the collateral flow channels, such as collagen and/or any derivative drug that promotes tissue growth.

In a first aspect of the present invention, methods for occluding collateral flow between adjacent lung segments comprise establishing a gas flow through the collateral flow channels in a wall between the at least two adjacent lung segments. Particles entrained in the gas flow lodge in the flow channels to occlude the collateral flow. Particles will typically have a size in the range from about 10 μm to 1000 μm, more usually from 50 μm to 500 μm. Preferably, the particles will be provided with a distribution of sizes within the above ranges in order to enhance the collection and lodging of the particles within the flow channels. In this way, flow channels having a variety of widths; lengths and geometries may be occluded.

In the exemplary embodiments, establishing the gas flow comprises sealing the distal end of the catheter in an airway feeding a hyperinflated or otherwise diseased lung segment. The catheter typically has a lumen or other passageway which provides an isolated passage between an exterior location (that is, outside of the patient) and the hyperinflated lung segment. Entraining typically comprises combining the particles with air, oxygen, an oxygen-helium mixture (heliox), NO, $NO_2$, or other carrier gas which is fed into the hyperinflated lung segment through the isolated passage in the catheter. Use of carrier gases having excess oxygen will be beneficial as it induces or promotes absorption atelectasis to reduce the volume of the target lung segment. Use of carrier gases having tissue dilating characteristics, such as NO or $NO_2$, promotes tissue gas diffusion to reduce the volume of the target lung segment.

The particles will be selected to be benign and biocompatible so that their implantation in the segmental wall will not induce an inflammatory or other harmful reaction over time. Moreover, it will be expected that at least some of the particles will become lodged within regions of the diseased or healthy lung segments, so the particles should also be compatible with long-term implantation within the alveoli. Suitable particle materials include silicones, polyurethanes, collagen, hydroxy apatites, sol-gels, ceramic based sol-gels, bone cements, hemo glues, and plasma surface can also be used. Exemplary suspension particles include PHEMA or other hydrogels that absorb water/mucus and expand to close the collateral channels. Furthermore, the particle materials may often be cross-linked and/or polymerized exposure to by external stimulation like X-ray, fluoroscopy, magnetic fields, infrared, ultraviolet, or the like. In other cases, the particle surface can be modified to induce tissue growth by exposure to glow discharge or other plasma treatment techniques. In still other cases, the particles will be selected to induce a benign inflammatory reaction. The use of such particles, however, will be generally less preferred.

The occluding particles will typically be drawn into the diseased or adjacent lung segment as the patient inhales. The particle delivery catheter will be positioned in the diseased or adjacent lung segment and/or in the airways feeding such segments. The catheter will include one or more dispersion ports or orifices for releasing the occluding particles into the targeted lung segments and establishing a circulation of the carrier gas through the collateral flow channels in the wall separating those segments. Excess particles may be removed through additional passageway(s) or lumen(s) in the particle delivery catheter, or alternatively or additionally may be simply exhaled through the airways which feed the lung segment(s). Usually, the inflow and outflow of the carrier gas will be established by the differential pressures created as the patient normally inhales and exhales. It would also be possible, however, to provide for pressurization of the carrier gas in order to promote inflow and dispersion of the particles through the delivery catheter and/or application of a vacuum in order to aspirate the carrier and other gases which carry the excess particles. In some instances, the particles may act as an aerosol adhesive when sprayed into the target area. As the target lung area deflates, the target lung area collapses and sticks together due to the particle adhesiveness, allowing no air to flow in from existing collateral channels. Alternatively, the particles can be introduced as a liquid or gel and can be polymerized to solidify and occlude the collateral channels and/or any other desired areas.

The delivery catheters will usually have a cuff, balloon, or other occluding element near their distal ends in order to isolate the diseased or other target lung segment as the particles are being introduced. Optionally, the delivery catheter may be introduced through a separate bronchoscope or other tubular introducer which also includes a cuff, balloon, or other occlusive element in order to isolate two or more of the adjacent lung segments at a point in the feeding airways upstream from the branch between the diseased and adjacent segment(s). Use of the bronchoscope permits further control of the flow particles among the two or more lung segments.

In a second aspect of the present invention, a system for occluding collateral flow between adjacent lung segments comprises a source of particles and a catheter. The source of particles comprises particles having a size and composition selected to lodge in and occlude collateral flow channels which may be present in the fibrous septum (wall) between adjacent lung segments. The catheter is adapted to be advanced through the airways of a lung and to deliver said particles to one of said adjacent lung segments. By delivering the particles, the collateral flow channels in the wall will become occluded by lodging of the particles as described above in connections with the methods of the present invention.

The particles preferably have a size and composition within the ranges set forth above, and further may have a generally spherical geometry, a generally irregular geometry, or may comprise particles having both such characteristics. The catheter may comprise a primary isolation catheter which includes at least one expandable occlusion element and at least one lumen extending from a proximal end of the catheter to a point distal of the occlusion element. Usually, the catheter will have at least one additional lumen extending from the proximal end to a point proximal to the occlusion element. The use of catheters having two lumens facilitates establishing a circulation of the particles by delivering the particles through one lumen and providing a return or exhalation path for the particles through the other lumen. Optionally, a secondary isolation catheter having a central passage for coaxially receiving the primary isolation catheter may be provided. A secondary isolation catheter preferably has an expandable occlusion element on or near its distal end, thus allowing isolation of two or more adjacent lung segments at a point upstream in the branching airways of the patient.

BRIEF DESCRIPTION OF THE DRAWINGS

FIGS. 7A-7C illustrate specific lung treatment protocols in accordance with the principles of the present invention.

DETAILED DESCRIPTION OF THE INVENTION

Figure 1:
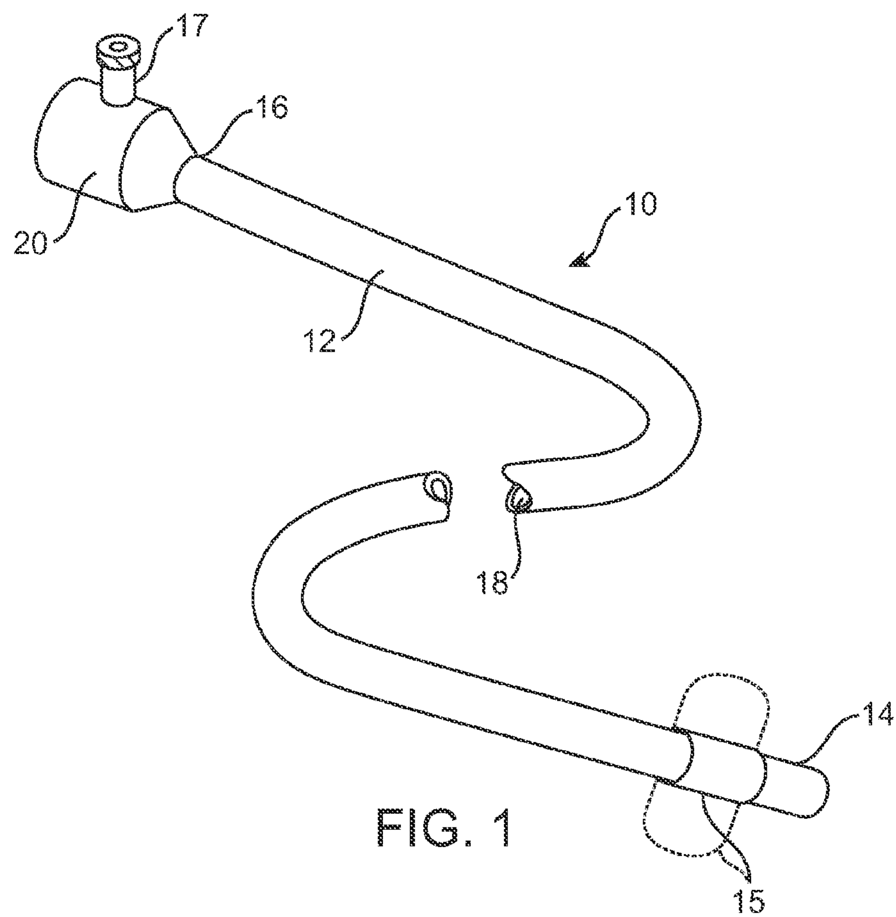
FIG. 1 is a perspective view of a particle delivery catheter constructed in accordance with the principles of the present invention.
Figure 2:
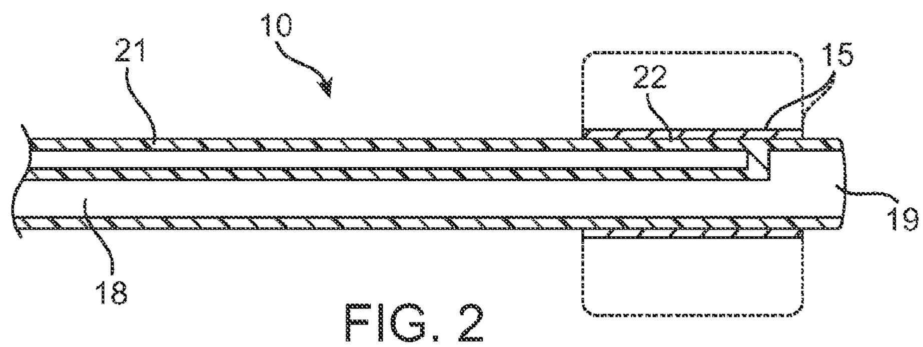
FIG. 2 is an axial, cross-sectional view of a distal portion of the catheter of FIG. 1, showing a single particle transfer lumen and a balloon inflation lumen.
Figure 3:
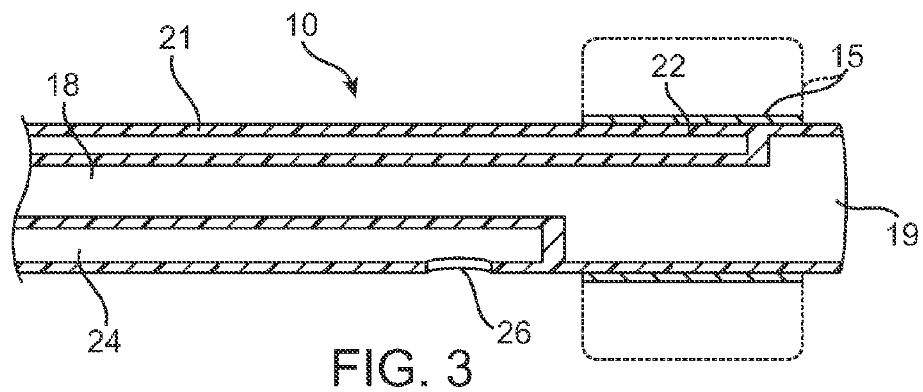
FIG. 3 is an alternative axial, cross-sectional view of the distal region of the catheter of FIG. 1, showing a separate particle introduction lumen and particle removal lumen.

Referring now to FIG. 1, an endobronchial particle delivery catheter 10 constructed in accordance with the principles of the present invention includes an elongate catheter body 12 having a distal end 14 and a proximal end 16 with an occlusion element 15, typically an inflatable balloon or cuff near the distal end or an expandable braided balloon as disclosed in copending, commonly owned applications Ser. No. 60/823,734, filed on Aug. 28, 2006, and Ser. No. 60,828,496, filed on Oct. 6, 2006, the full disclosures of which are incorporated herein by reference. Catheter body 12 includes at least one central lumen or passage 18 with a distal opening 19 (FIGS. 2 and 3). A hub 20 is disposed at the proximal end 16 of the catheter body 12 and includes at least one port 17 for connection to an inflation lumen 21 which feeds an inflation medium to the expandable element 15, for sealing the distal end of the catheter within a lung airway.

In a first specific embodiment of the catheter 10, only a single central lumen or passage 18 is provided for delivery of occlusive particles, as described in greater detail hereinafter. The balloon inflation lumen 21 opens through a port 22 to deliver the inflation medium to the expandable member 15. A second embodiment of the catheter 10 has the central lumen or passageway 18 and a second lumen or passageway 24 which terminates in at least one side port 26 for delivering and/or receiving the flow of particles, as described in more detail below.

The endobronchial particle delivery catheters have a length in the range from about 20 cm to about 200 cm, preferably from 80 cm to 120 cm, and a diameter or width near the distal end selected to allow entry of the distal end into the airways leading to the lung segments, typically being in the range from 0.1 mm to 10 mm, preferably from 1 mm to 5 mm. The expandable occluding member 15 will typically be an inflatable balloon or cuff, where the balloon or cuff has a width in the range from 1 mm to 30 mm, preferably from 5 mm to 20 mm, when inflated. The catheter body may be composed of conventional catheter materials to provide the desired flexibility and biocompatibility. Suitable materials include PTFE, PVC, polyurethane, PET, polypropelene or other polymer alloys or interpenetrating network polymers (IPNs) with or without metallic and/or ceramic braid or support. Using such materials, the catheters may be formed by conventional extrusion techniques.

Although not illustrated, the catheters 10 may be provided with other capabilities, such as the addition of pull wires or other mechanisms for steering the distal ends of the catheters in order to facilitate advancement through the branching airways of the lung. Still further additionally, the catheters 10 may be provided with optical fibers, small CCD's or other cameras, or other means at their distal ends for visualizing advancement of the catheters through the airways.

Figure 4:
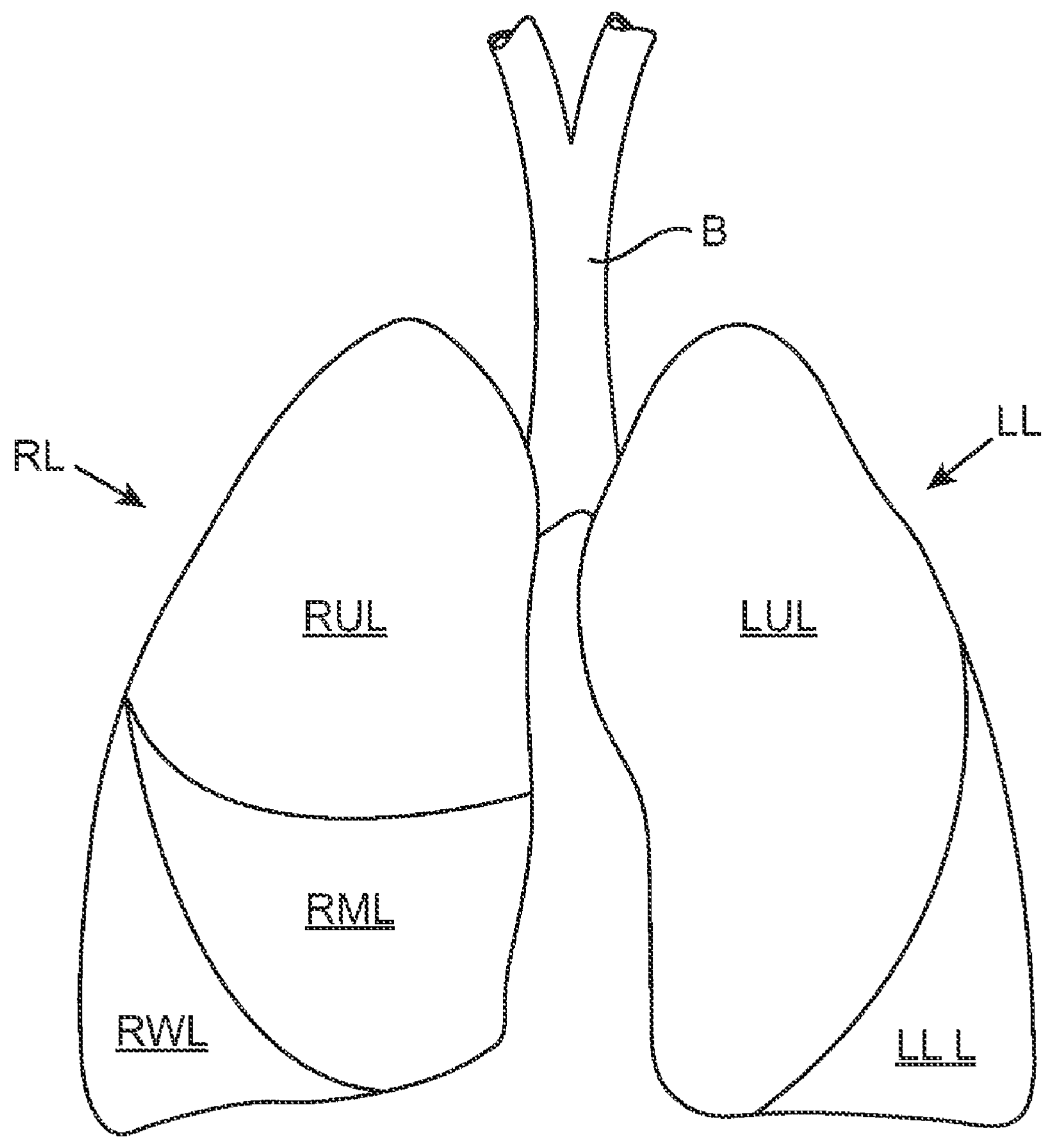
FIG. 4 is an anatomical diagram illustrating the lobar structure of the lungs of a patient.

Referring now to FIG. 4, the respiratory system of the patient starts at the mouth and extends through the vocal cords and into the trachea where it then joins the main stem bronchi B which leads into the right lung RL and the left lung LL. The bronchi going into the right lung divide into the three lobar bronchi which lead into the upper lobe RUL, the middle lobar RML and the lower lobar RLL. The lobes of the right lung each include ten segments which are discrete units of the lung separated from each other by a fibrous septum generally referred to as a lung wall. The left lung LL includes only an upper lobe LUL and a lower lobe LLL, where the individual lobes include eight or nine segments.

Each lung segment, also referred to as a bronchopulmonary segment, is an anatomically distinct unit or compartment of the lung which is fed air by a tertiary bronchus and which oxygenates blood through a tertiary artery. Normally, the lung segment and its surrounding fibrous septum are intact units which can be surgically removed or separated from the remainder of the lung without interrupting the function of the surrounding lung segments.

The presence of collateral flow channels in the fibrous septum or wall of a diseased lung segment is problematic since the diseased segment cannot be removed or even isolated successfully with the collateral channels intact. In the case of isolation and deflation of the diseased lung segment, the presence of the collateral channels will permit the reentry of air as the patient breathes. Thus, the present invention, by occluding the collateral passages, returns a perforate or porous lung wall into a functionally intact lung wall which permits subsequent treatment of diseased regions using endobronchial or other treatment protocols.

Figure 5:
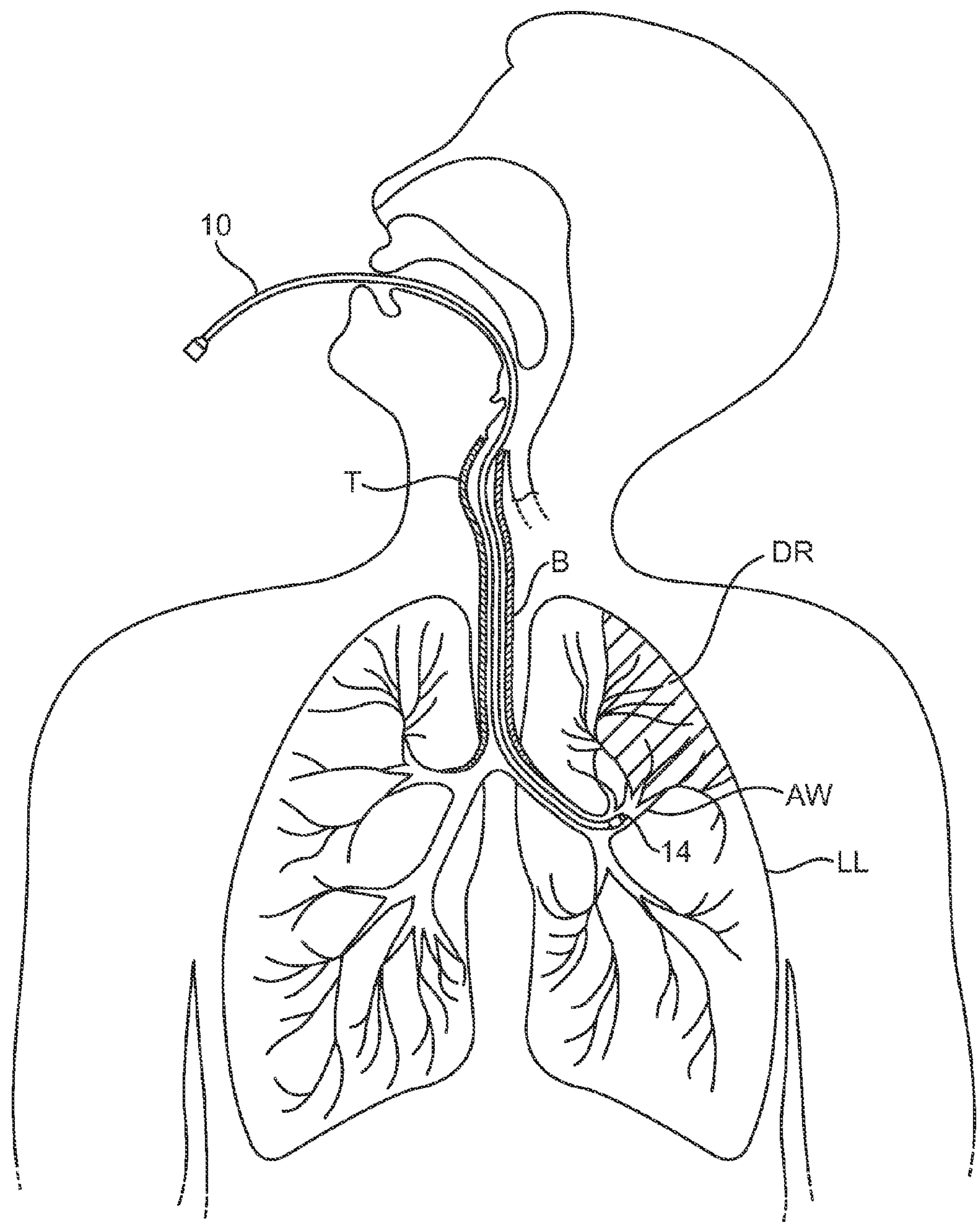
FIG. 5 illustrates the trans-esophageal endobronchial placement of a particle delivery catheter in an airway leading to a diseased lung region having adjacent lung segments which may be treated in accordance with the principles of the present invention.
Figure 6A:
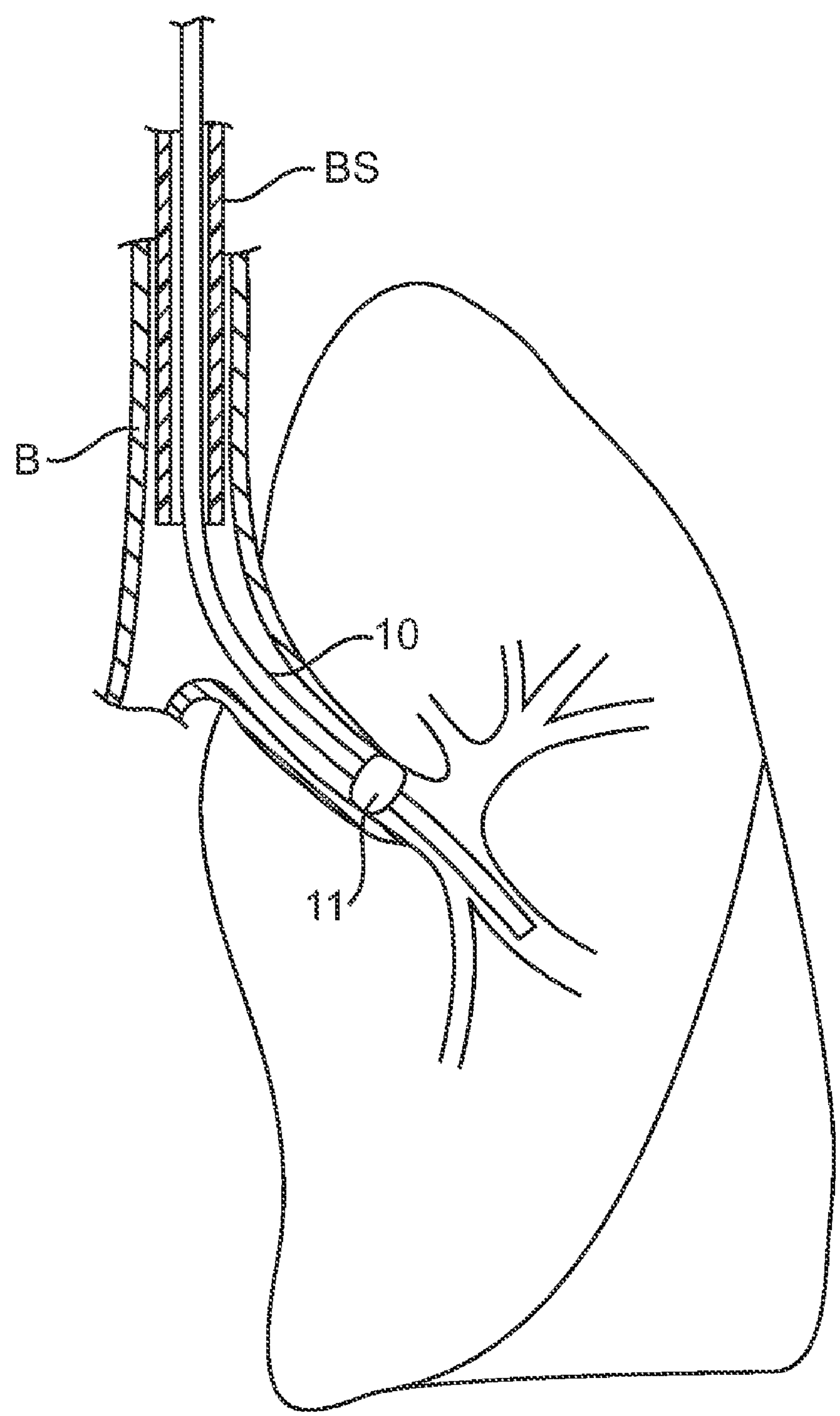
FIGS. 6A and 6B illustrate alternative catheter introduction protocols in accordance with the principles of the present invention.
Figure 6B:
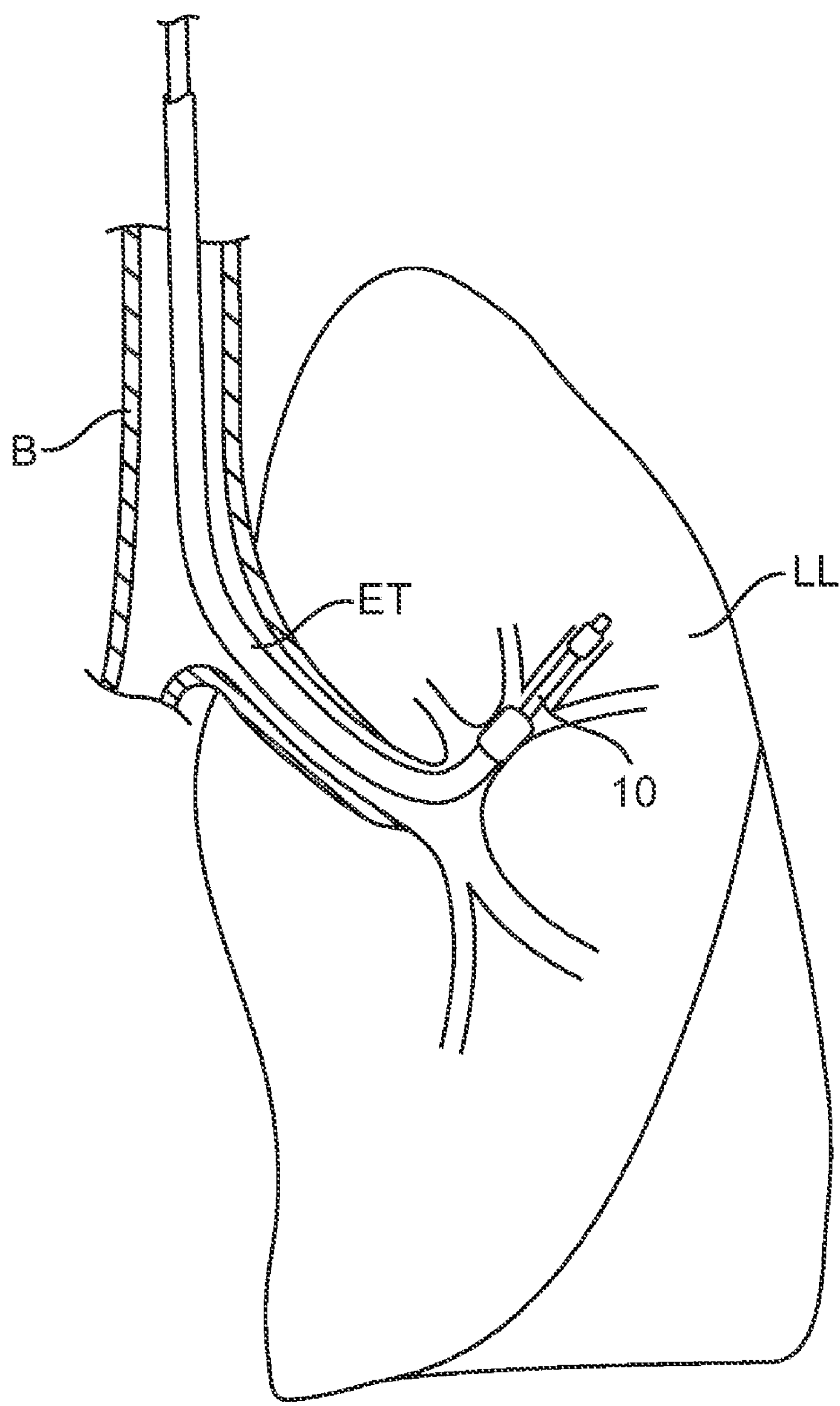

Use of the endobronchial particle delivery catheter for treating collateral flow between adjacent lung segments begins with the endotracheal introduction of the catheter, as shown generally in FIG. 5. The catheter 10 is advanced through the mouth, down through the trachea, and through the main bronchus into the left lung LL. The distal end 14 of catheter 10 is advanced into the left lung, and further advanced to a target lung segment as will be described in more detail in connection with FIGS. 7A-7C. The catheter 10 may be introduced through the main bronchus B and into the left lung LL without the use of a bronchoscope or other primary introducing catheter, as shown in FIG. 5. Alternatively, as shown in FIG. 6A, catheter 10 may be introduced through a conventional bronchoscope BS. Alternatively, the catheter 10 may be introduced into the lung through a scope, such as a visualizing endotracheal tube ET or bronchoscope with an inflatable cuff C which isolates an area of the lungs and permits local control of breathing, lung pressurization, and the like, as shown in FIG. 6B. Use of such a scope which is capable of advancing into the branching airways of the lung is advantageous in that it facilitates positioning of the particle delivery catheter 10 at the desired airway leading to a target lung segment. Optionally, catheter 10 may have an occlusion cuff or balloon 11 near its distal end to anchor the catheter. Construction and use of a visualizing endotracheal tube is taught, for example, in U.S. Pat. No. 5,285,778, the full disclosure of which is incorporated herein by reference. It would be possible, of course, to utilize both the bronchoscope BS and the endotracheal tube ET in combination for positioning the particle delivery catheter 10 in the desired lung segment airway.

Figure 7A:
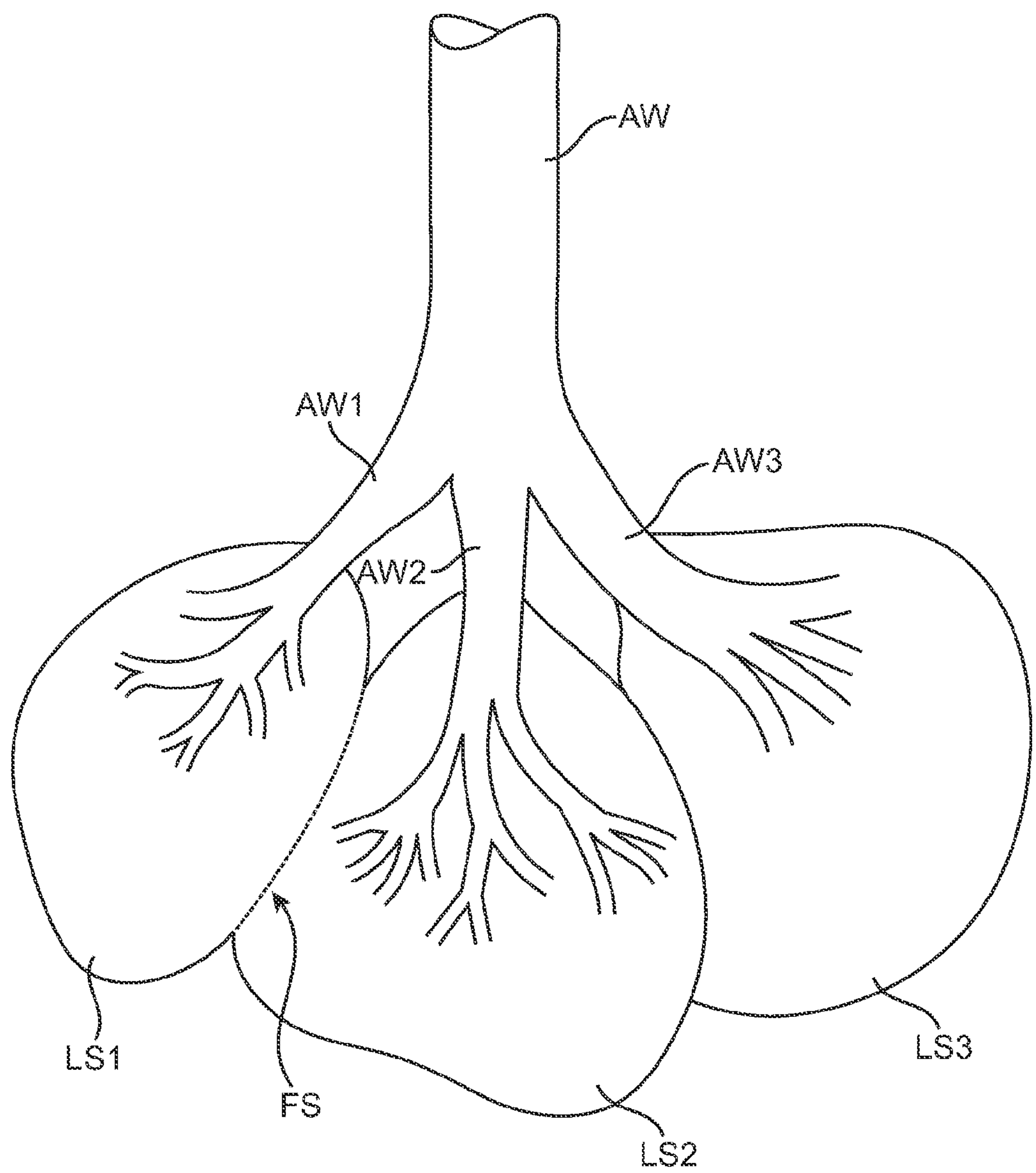

Referring now to FIG. 7A, the individual lobes of a lung each comprise a plurality of lung segments LS which are fed by individual branches of the bronchi or airways AW. For example, a first lung segment LS1, a second lung segment LS2, and a third lung segment LS3 may be fed from a single airway AW which divides into three branches AW1, AW2, and AW3, as illustrated in FIG. 7A. In healthy lungs, the septa between the lung segments will be intact and will maintain the pneumatic isolation of the segments. In the cases of diseased or other compromised lung segments, however, the fibrous septum may be perforate or porous to provide collateral flow channels therebetween, as illustrated at FS in FIG. 7A. It is the purpose of the present invention to occlude the flow channels in the wall with particles by entraining the particles in an air or other carrier gas flow between the adjacent segments to cause the particles to lodge in the channels.

Figure 7B:
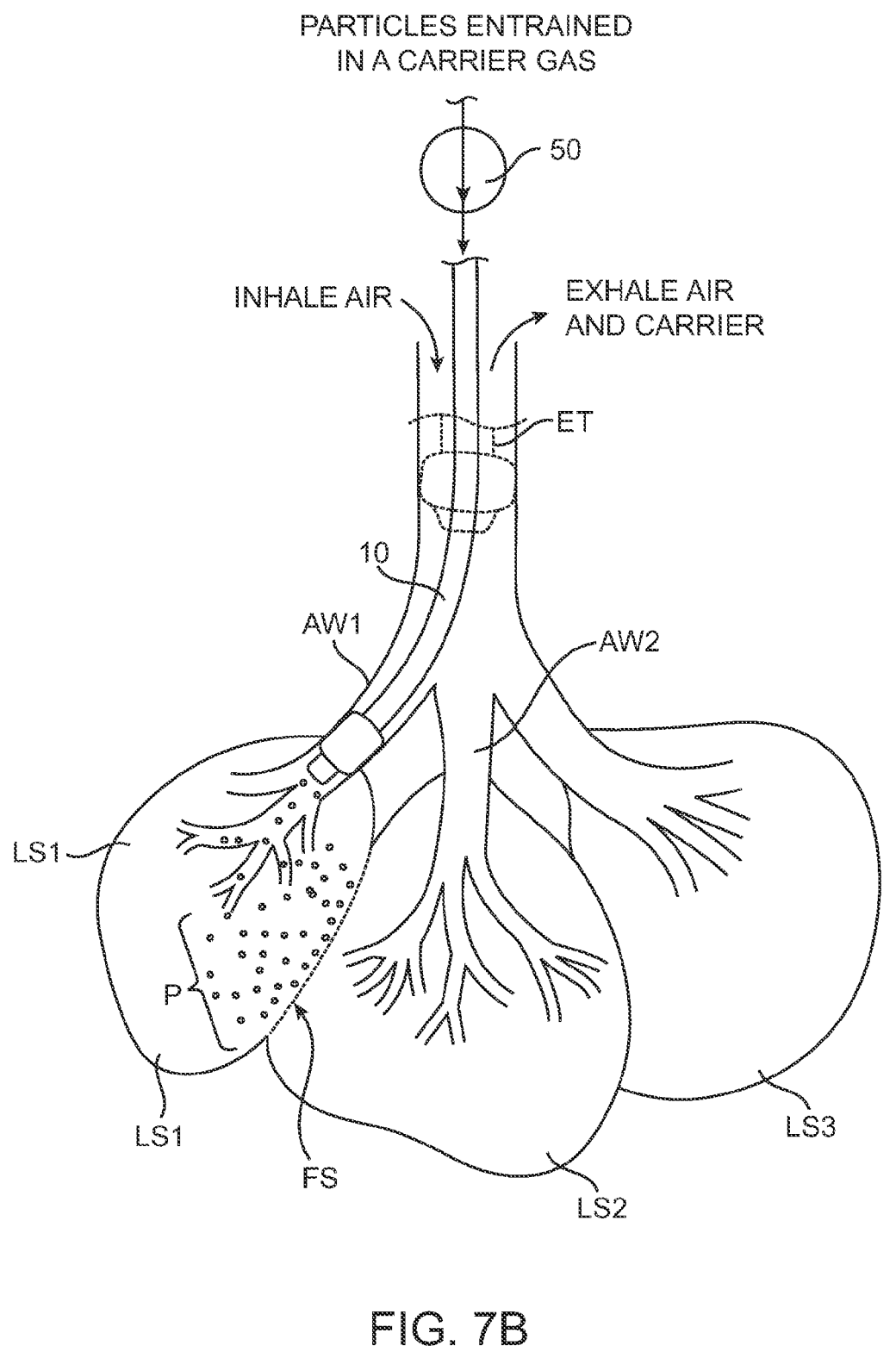

Referring now to FIG. 7B, the catheter 10 having only a single central lumen or passage 18 (FIG. 2) is positioned in airway 1 AW1 leading into lung segment 1 LS1, which may be a diseased lung segment or may be adjacent to a diseased lung segment. The collateral channels in the wall FS between the first lung segment LS1 and the second lung segment LS2 will permit gas flow in either direction prior to the treatments of the present invention. By expanding the expandable member 15 in the first airway AW1, the first lung segment LS1 is isolated, which isolation is compromised only by the collateral flow channels. By introducing particles P through the central lumen or passage 18 of the catheter 10 into the lung segment 1, they may be carried into the pores, to thus occlude the pores, as the patient breathes. This is accomplished, for example, by providing a one-way flow structure 50 attached to the hub 20 of the catheter 10 so that air and particles only enter the first lung segment LS1 as the patient inhales. As the patient exhales, the one-way flow element 50 prevents air (and particles) from flowing back through the central passage or lumen 18, and causing the particles to flow outwardly through the flow channels in the wall FS. At least some of the particles which enter the flow channels will become lodged in the flow channels and will, with the buildup of particles, occlude the flow channels over time. Those particles which escape into the second lung segment LS2 will be naturally exhaled by the patient. Optionally, an endotracheal tube ET (shown in broken line) may be positioned in the airway upstream from the first airway AW1 in order to help collect the particles being exhaled from the second lung segment LS2 and prevent those from entering other regions of the lung.

It will be appreciated that the catheter 10 could also have been placed in the second airway AW2 in order to deliver particles into the collateral flow channels and wall FS. The use of the endotracheal tube ET would also permit aspiration of the particles and/or the use of positive pressure through the catheter 10 and aspiration through the endotracheal tube ET.

Figure 7C:
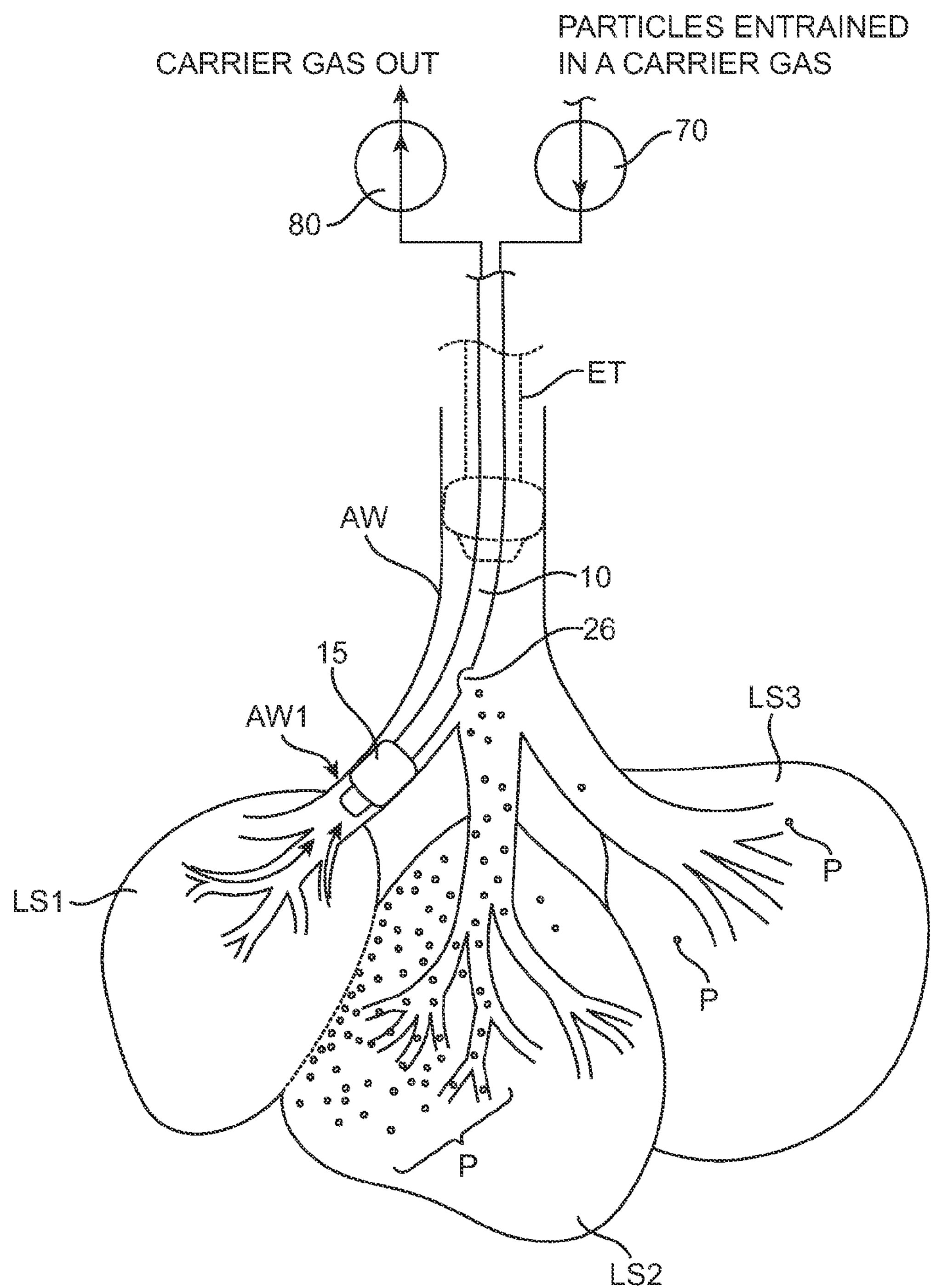

Referring now to FIG. 7C, the catheter 10 having first and second central lumens 18 and 24 (FIG. 3) for delivering and removing particles will be described. Expandable member 15 is expanded within the first airway AW1 and particles are introduced through the second lumen or passage 24 and dispersed out of the side port 26 so that they will primarily enter the second lung segment LS2. Some particles, of course, will also enter the third lung segment LS3 as they will be entrained in the air or other carrier gas as the patient inhales. When the patient exhales, air will flow out through the first passage 18 of the catheter 10. Usually, a one-way flow element 70 will be provided to permit the air or other carrier gas to enter the second lumen or passageway 24 to disperse the particles P, but prevent the carrier gas from exiting through the port while the patient exhales. Preferably, an endotracheal tube ET (shown in broken line) will be provided to further prevent exit of the particles from the second lung segment LS2, although such further occlusion is not necessary.

As the patient exhales, air or other carrier gas in the first lung segment LS1 will flow outwardly through the first central lumen or passageway 18, preferably, a second one-way flow element 80 is provided which permits such outflow of carrier gas through the lumen 18 but which permits such outflow of carrier gas through the lumen 18 but which prevents the inflow gas when the patient inhales. Thus, catheter 10 as illustrated in FIG. 3 provides a local circulatory path from a first lung segment, through the collateral channels and an intermediate wall or fibrous septum, and out through the adjacent lung segment. By further isolating the two adjacent lung segments, the circulation of the occluding particles may be further limited to those two segments and possibly other segments which branch from the same common airway AW.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for occluding collateral flow channels between adjacent lung segments, said method comprising:
- providing a distribution of particles having a composition and a range of sizes from 100 μm to 1000 μm selected to lodge in and occlude the collateral flow channels;
- establishing a gas flow through the collateral flow channels in a wall between the at least two adjacent lung segments; and
- entraining the particles in said gas flow, wherein the particles lodge in the flow channels to occlude collateral flow.

2. A method as in claim 1, wherein the particles are composed at least partly from a material selected from the group consisting of silicones, polyurethanes, collagen, hydroxy apatites, sol-gels, ceramic sol-gels, bone cements, and hemo glues.

3. A method as in claim 1, wherein the particles are composed of a hydrogel.

4. A method as in claim 1, wherein the particles have a surface that has been modified to induce an inflammatory response when implanted.

5. A method as in claim 1, wherein the collateral channels have walls, and the particles induce adherence of the walls of the collateral channels to close and adhere.

6. A method as in claim 1, wherein the particles release a drug which promotes tissue ingrowth.

7. A method as in claim 6, wherein the drug is selected from the group comprising collagen and/or any derivative drug that promotes tissue growth.

8. A method as in claim 1, wherein establishing comprises:
- sealing a distal end of a catheter in an airway feeding a target lung segment, wherein the catheter provides an isolated passage between the target lung segment and an exterior location.

9. A method as in claim 8, wherein entraining comprises:
- combining the particles with a carrier gas being fed into the target lung segment through the isolated passage in the catheter.

10. A method as in claim 9, wherein the carrier gas comprises excess oxygen to induce or promote absorption atelectasis.

11. A method as in claim 10, further comprising exhaling through a path which bypasses isolated passage in the catheter.

12. A method as in claim 11, wherein the bypass path is through a separate passage in the catheter.

13. A method as in claim 11, wherein the bypass path is through an annular region surrounding the catheter.

14. A method as in claim 8, wherein entraining comprises:

combining the particles with a carrier gas being fed to a lung segment adjacent to the target lung segment, wherein the carrier gas carries the particles into the collateral flow channels and the gas is exhaled at least partially through the isolated passage.

15. A method as in claim 14, wherein the carrier gas is introduced through a second passage in the catheter which releases the carrier gas upstream of the sealed distal end of the catheter.

16. A method as in claim 14, further comprising blocking all gas flow to and from the target and adjacent lung compartment(s) other than through the catheter passage(s).

17. A method as in claim 16, wherein blocking comprises inflating a cuff on a bronchoscope, wherein the catheter passes through a passage in the bronchoscope.

* * * * *